United States Patent
Wang

(10) Patent No.: US 10,603,148 B2
(45) Date of Patent: Mar. 31, 2020

(54) POWERED TOOTHBRUSH WITH BRISTLES HAVING RANDOM MOTION

(71) Applicant: INNOTECH APPLIANCE LIMITED, Kowloon (HK)

(72) Inventor: Hai Wang, Kowloon (HK)

(73) Assignee: INNOTECH APPLIANCE LIMITED, Kowloon (HK)

(*) Notice: Subject to any disclaimer, the term of this patent is extended or adjusted under 35 U.S.C. 154(b) by 140 days.

(21) Appl. No.: 15/982,711

(22) Filed: May 17, 2018

(65) Prior Publication Data

US 2018/0333241 A1    Nov. 22, 2018

Related U.S. Application Data

(63) Continuation-in-part of application No. 15/633,609, filed on Jun. 26, 2017.

(30) Foreign Application Priority Data

May 17, 2017    (CN) ............ 2017 2 0550094 U

(51) Int. Cl.
*A47L 11/00* (2006.01)
*A61C 17/34* (2006.01)

(52) U.S. Cl.
CPC ........ *A61C 17/3472* (2013.01); *A61C 17/349* (2013.01); *A61C 17/3418* (2013.01);
(Continued)

(58) Field of Classification Search
USPC .............. 15/22.1, 22.2, 28, 167.1, 201
See application file for complete search history.

(56) References Cited

U.S. PATENT DOCUMENTS

| 6,161,245 A | * | 12/2000 | Weihrauch | ............ A46B 7/06 15/167.1 |
| 6,553,604 B1 | * | 4/2003 | Braun | ............ A46B 9/04 15/167.1 |

(Continued)

FOREIGN PATENT DOCUMENTS

| JP | H05 76416 A | 3/1993 |
| WO | 2012/035490 A1 | 3/2012 |

OTHER PUBLICATIONS

Extended European Search Report dated Nov. 9, 2017 issued in connection with related European Patent Application No. 17173239.9 (8 pages total).

*Primary Examiner* — Joseph J Hail
*Assistant Examiner* — Shantese L McDonald
(74) *Attorney, Agent, or Firm* — Mark K. Young; Mayer & Williams PC

(57) ABSTRACT

A powered toothbrush includes a plurality of rows of bristle tufts that project through a perforated top shell of a hollow toothbrush head. Ends of individual bristles are held in buckets to form the tufts and the bristle ends opposite the bucketed ends are free (where the opposite ends contact the toothbrush user's teeth). The bucketed ends of the bristle tufts are captured within the internal space within the head but are not fixedly attached to any other toothbrush component or structure. This non-fixed attachment feature enables the bristle tufts to have multiple degrees of freedom (DoF) of motion with respect to the perforations in the top shell and can rotate, move axially, and tilt.

20 Claims, 7 Drawing Sheets

(52) U.S. Cl.
CPC ...... *A61C 17/3436* (2013.01); *A61C 17/3463* (2013.01); *A61C 17/3481* (2013.01)

(56) References Cited

U.S. PATENT DOCUMENTS

| | | |
|---|---|---|
| 2004/0168269 A1 | 9/2004 | Kunita et al. |
| 2005/0060822 A1 | 3/2005 | Chenvainu et al. |
| 2014/0245553 A1* | 9/2014 | Gravina .................. A46B 9/04 15/167.1 |

* cited by examiner

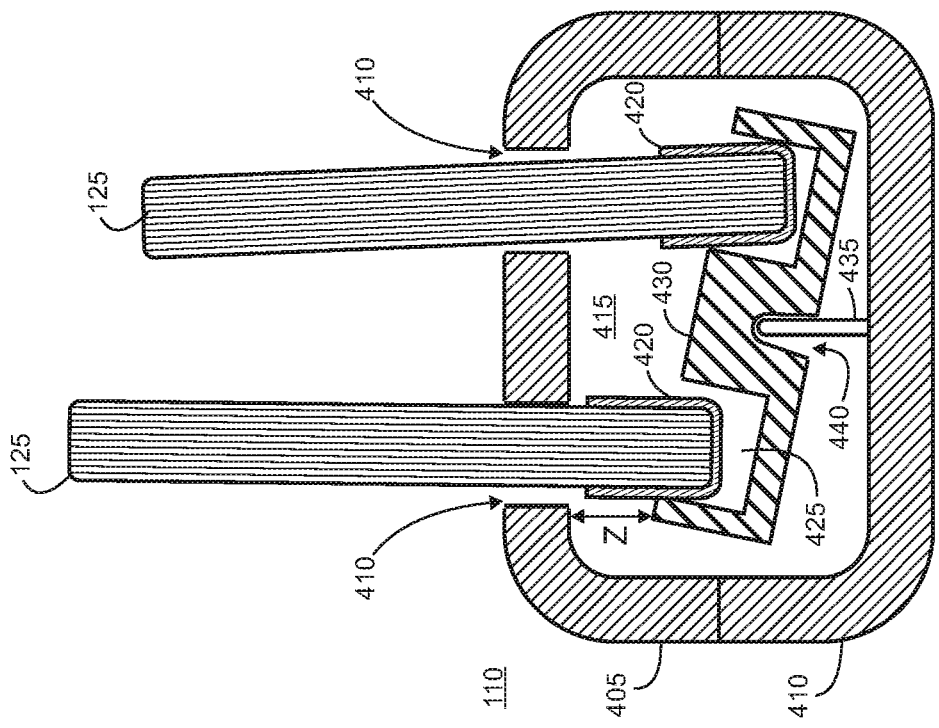
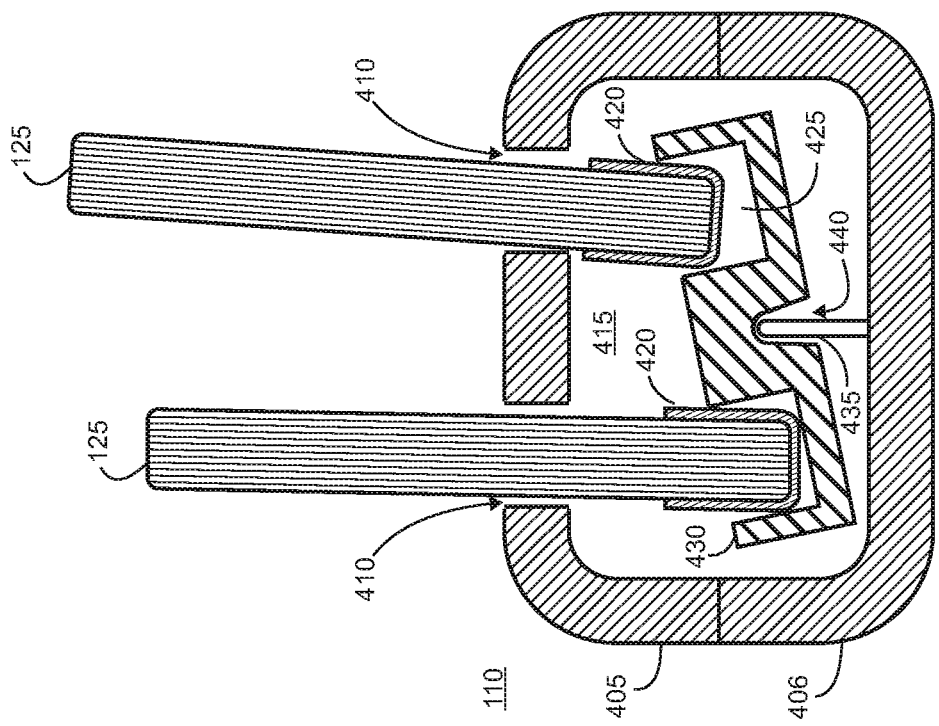

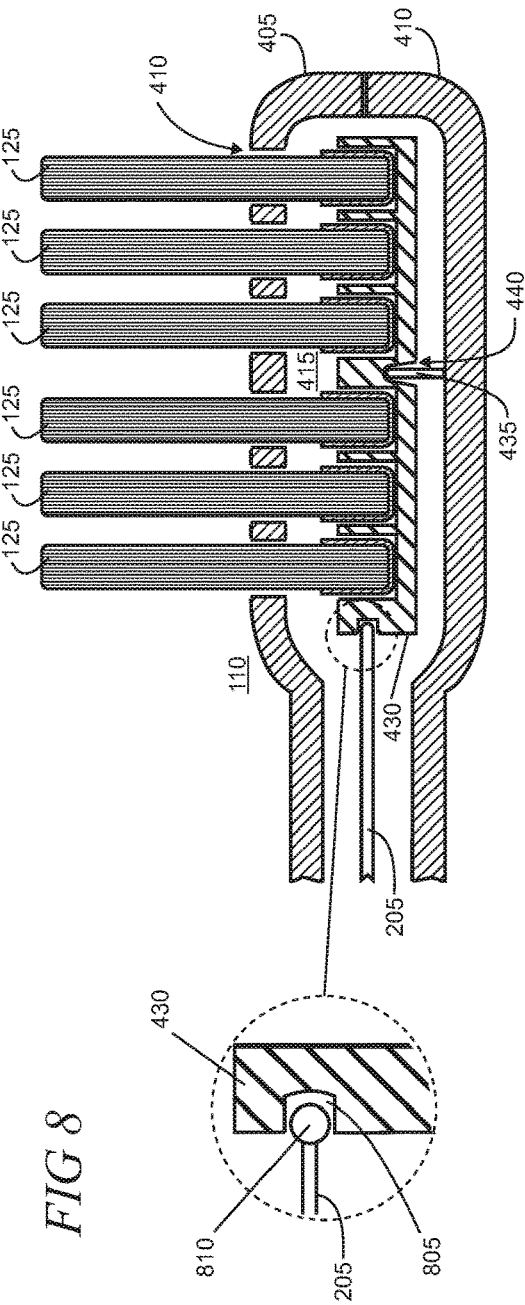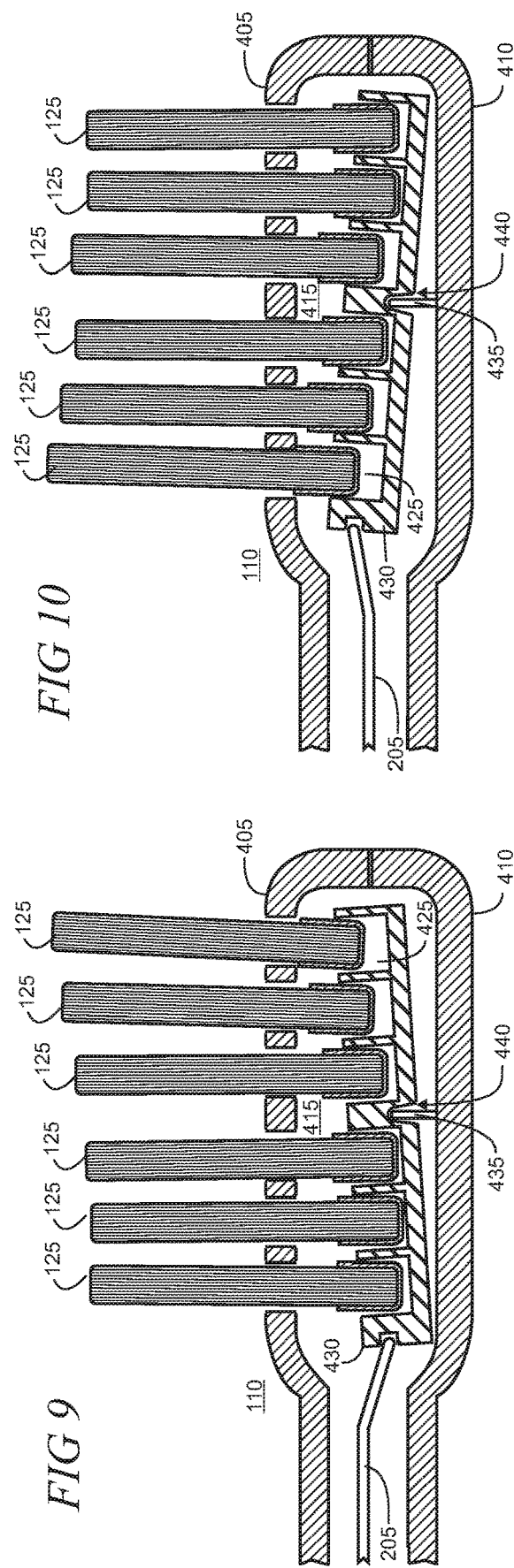
FIG 8
FIG 9
FIG 10

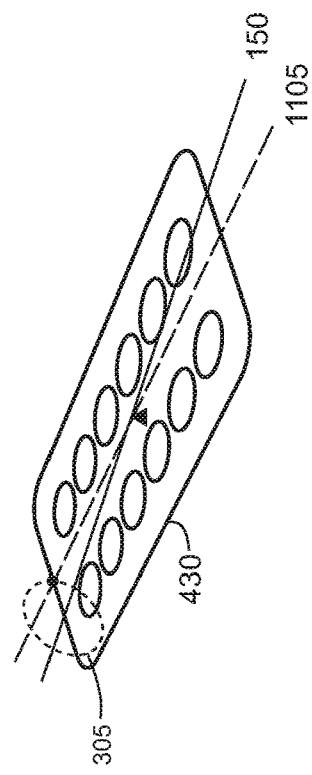
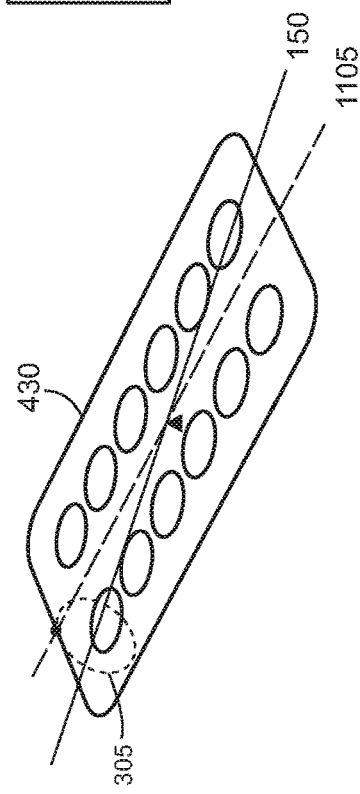
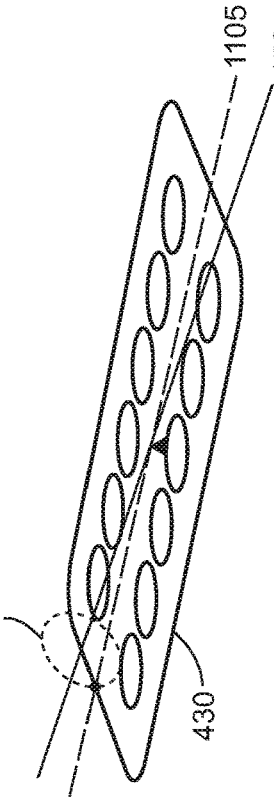
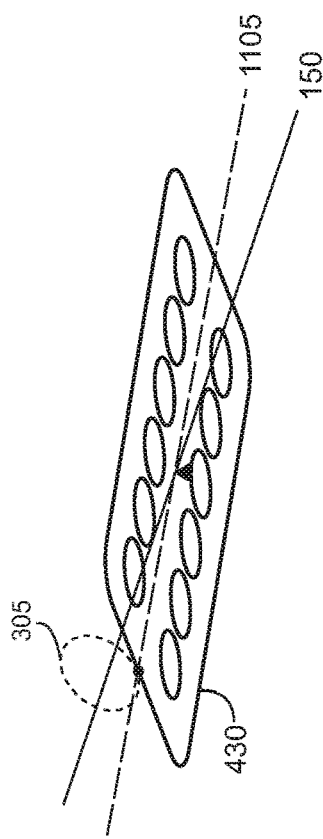
FIG 11A
FIG 11B
FIG 11C
FIG 11D

POWERED TOOTHBRUSH WITH BRISTLES HAVING RANDOM MOTION

STATEMENT OF RELATED APPLICATIONS

This application is a continuation in part of U.S. Ser. No. 15/633,609, filed Jun. 26, 2017, entitled "A TOOTHBRUSH DEVICE" and claims benefit and priority to Chinese Patent No. CN202636545U filed May 17, 2017, entitled "A Toothbrush Device" which is incorporated herein by reference in its entirety.

BACKGROUND

Conventional powered toothbrushes have teeth cleaning elements (such as bristles) that are fixedly attached and extend from a head such that the motion of elements with respect to the head follow a prescribed path. Teeth and gums by nature have a complex intricate contour. Due to the prescribed motion of the tooth cleaning elements and fixed attachment with respect to the head of the toothbrush, the orientation of the teeth cleaning elements is not flexible and thus conventional powered toothbrushes do not provide optimal cleaning of teeth and gums. Conventional powered toothbrushes therefore have great difficulty in contacting areas of the teeth located at a greater distance from the head, including interproximal spaces between teeth.

SUMMARY

A powered toothbrush includes a plurality of rows of bristle tufts that project through a perforated top shell of a hollow toothbrush head. Ends of individual bristles are held in buckets to form the tufts and the bristle ends opposite the bucketed ends are free (where the free opposite ends contact the toothbrush user's teeth). The bucketed ends of the bristle tufts are captured within the internal space of the head but are not fixedly attached to any other toothbrush component or structure. This non-fixed attachment feature enables the bristle tufts to have multiple degrees of freedom (DoF) of motion with respect to the perforations in the top shell and can rotate, move axially, and tilt.

The outer bottom and side surfaces of the bucket are configured to interface with bucket recesses in a movable plate that tilts and rotates about a fixed pivot as it is driven by a drive mechanism. The top circumferential edge of the bucket (i.e., the bucket's "rim") is configured as a stop that engages with the inside surface of the top shell to limit axial excursion of the bristle tufts. That is, the diameter of the bucket exceeds that of the perforations in the top shell.

The movable plate is tiltably and rotatably mounted on the inside bottom shell of the hollow toothbrush head. The movable plate tilts and rotates on a pivot point that extends upwards from the bottom shell to interact with the plate around or at its center. One end of the movable plate includes a driveshaft receiving portion that is configured for movable engagement with the drive mechanism. The follower may comprise a recess that is configured to receive the tip of the free end of a drive rod that is rotatably driven about its longitudinal axis by a user-switchable motor. A portion of the free end is bent so that the tip of the rod is offset relative to its longitudinal axis. Thus, as the rod is driven, the tip of the rod traverses a circular path in a plane that is orthogonal to the longitudinal axis.

When the motor is operated, the movable plate tilts (i.e., rocks) and rotates with respect to the stud as the follower follows the circular path of the rod tip. The recesses in the plate are sized to enable the bucketed bristle tufts to slideably move freely with respect to the plate. The plate recesses match the top shell perforations in number and arrangement. During motor operation, the tilting and rotating of the plate causes the centers of the recesses and the perforations to be cyclically obliquely and non-obliquely aligned. Accordingly, the free ends of the bristle tufts tilt in different directions and move up and down with respect to the outside surface of the upper shell as the powered toothbrush is operated.

The movable plate and internal space in the toothbrush head are configured so that the bucketed bristle tufts have space for motion that is independent from the plate motion. The bucketed bristles are free to move in the internal space which has dimensions that exceed the total excursion of the movable plate. As the bucketed bristles are not fixedly attached to the movable plate, the bristle motion can at least be partially independent from the plate as the powered toothbrush is operated. This partial independence gives rise to random motions of one or more of the bristle tufts during periods of toothbrush operation.

In one illustrative embodiment, the movable plate is driven with a suitable and relatively high frequency to cause vibratory motion of the plate. The movable plate when operated in this manner collides with the buckets to impart a sharp force that accelerates the bucket in the direction of the force application. The tilting and rotating motion of the movable plate is such that the plane of the plate is not always parallel to the plane of the bottom of the bucket. Accordingly, the point of contact between the movable plate and the buckets can vary. Such variation can cause, by itself or in combination with other factors (e.g., bristle motions caused by interactions with the user's teeth), periods of random motion for the bristles during toothbrush operation.

Substantial advantage is achieved by providing a powered toothbrush with bristle tufts that are driven with random motion. In particular, certain embodiments improve cleaning of teeth and gums, and provide improved access to and contact with areas of the teeth located at a distance from the toothbrush head, including interproximal spaces between the teeth. These and additional features and advantages disclosed herein will be further understood from the following detailed disclosure of certain embodiments.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Furthermore, the claimed subject matter is not limited to implementations that solve any or all disadvantages noted in any part of this disclosure. These and various other features will be apparent from a reading of the following Detailed Description and a review of the associated drawings.

DESCRIPTION OF THE DRAWINGS

FIGS. 4, 5, 6, and 7 show the illustrative powered toothbrush in a sectional view taken along A-A in FIG. 1;

FIGS. 8, 9, and 10 show the illustrative powered toothbrush in a sectional view taken along B-B in FIG. 1; and FIGS. 11A, 11B, 11C, and 11D show a movable plate having recesses for bucketed bristle tufts in various orientations including combinations of tilting and rotation as it is driven by a coupled drive assembly.

The invention may take form in various components and arrangements of components, and in various procedures and arrangements of procedures. The drawings are only for purposes of illustrating preferred embodiments, they are not to scale, and are not to be construed as limiting the invention.

DETAILED DESCRIPTION

Figure 1:
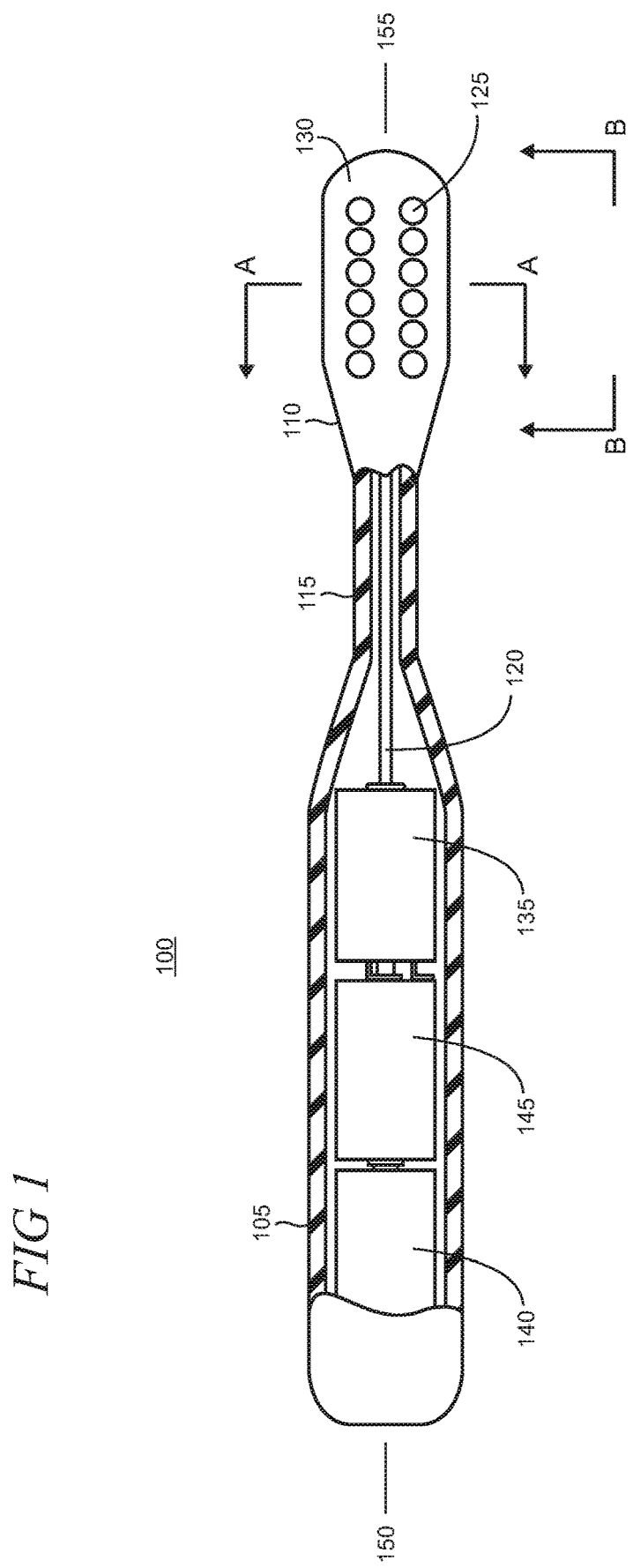
FIG. 1 shows an illustrative example of a powered toothbrush with bristles having random motion in accordance with the principles of the present invention, shown in a partially sectional view.
Figure 2A:
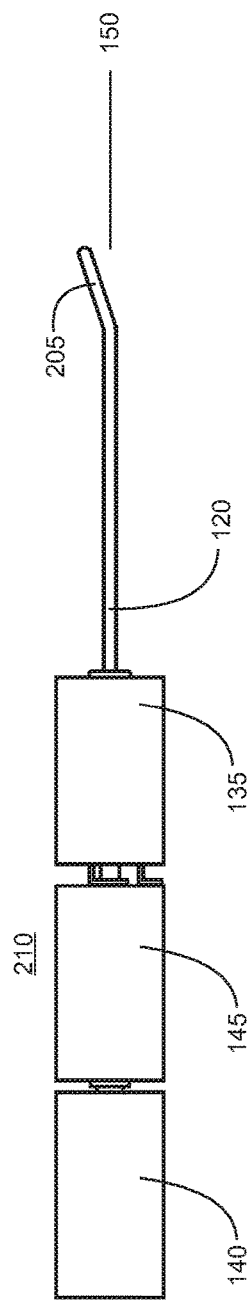
FIGS. 2A, 2B, 2C, and 2D sequentially show the driveshaft as it rotates through one revolution.
Figure 2B:
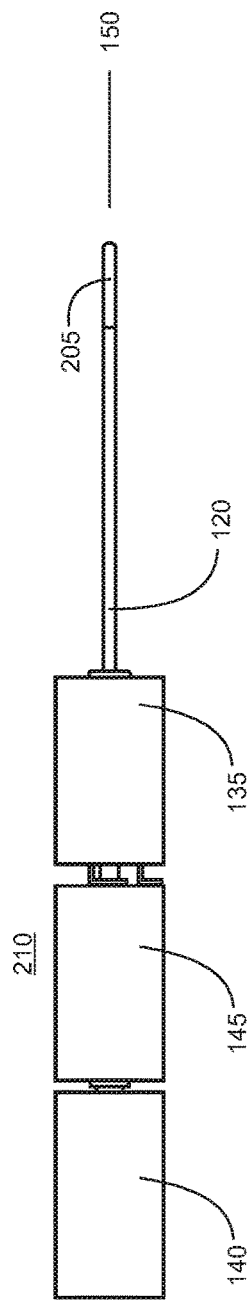
Figure 2C:
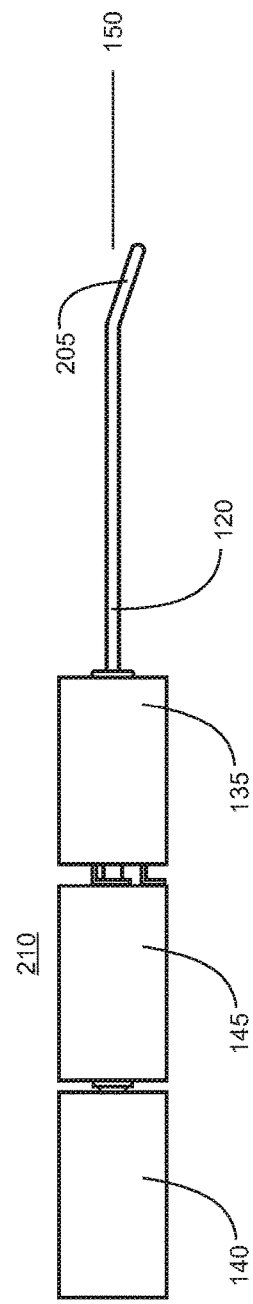
Figure 2D:
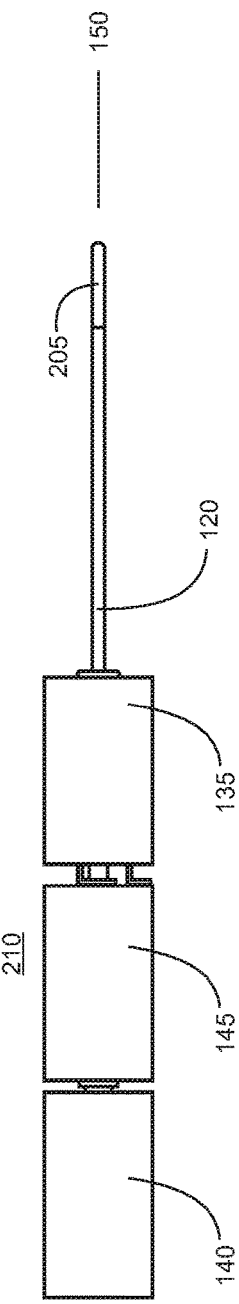

Referring to the drawings, in FIG. 1 the present powered toothbrush 100 comprises a handle 105 at a proximal end of the toothbrush, a head 110 at a distal end of the toothbrush, a neck 115 extending therebetween, a rotatable driveshaft 120 extending from the handle to the head, and a plurality of bristle tufts (representatively indicated by reference numeral 125) extending through perforations in a shell 130 of the head, wherein each tuft comprises a plurality of bristles. The handle provides compartments for holding an electric motor 135 that receives electric power from a power source such as batteries 140 and 145. In typical implementations, the batteries are configured to be rechargeable by a battery charger (not shown) that can be coupled to a household power circuit such as a wall outlet. In alternative implementations, an internal power supply (not shown) that interfaces directly with the household power circuit can be used to supplement or substitute for the batteries. Two batteries are shown in FIG. 1, but fewer or more batteries can used, and the toothbrush can also be adapted to utilize non-rechargeable or disposable batteries.

The motor 135 can be configured to operate at fixed speed or multiple different speeds which may be selectable by the toothbrush user through, for example, a switch (not shown). The driveshaft 120 has a longitudinal axis 150 that is generally parallel to the longitudinal axis of the toothbrush 100, where, in this illustrative example, the handle 105 and neck 115 share a common longitudinal axis. The head 110 has a longitudinal axis 155 that may also share the common axis in some embodiments. The driveshaft may be supported by supports or bearings (not shown) in the handle, neck, and/or head.

The bristle tufts 125 are arranged to extend through circular perforations in the head 110, although other perforation shapes are contemplated as falling within the scope of the present invention. The bristle tufts, as shown in this illustrative example, are arranged in two rows of six bristle tufts. However, this is merely illustrative, as other numbers of rows and bristle tufts may also be utilized, and the rows can be staggered, non-staggered, or be arranged in combinations thereof.

Figure 3:
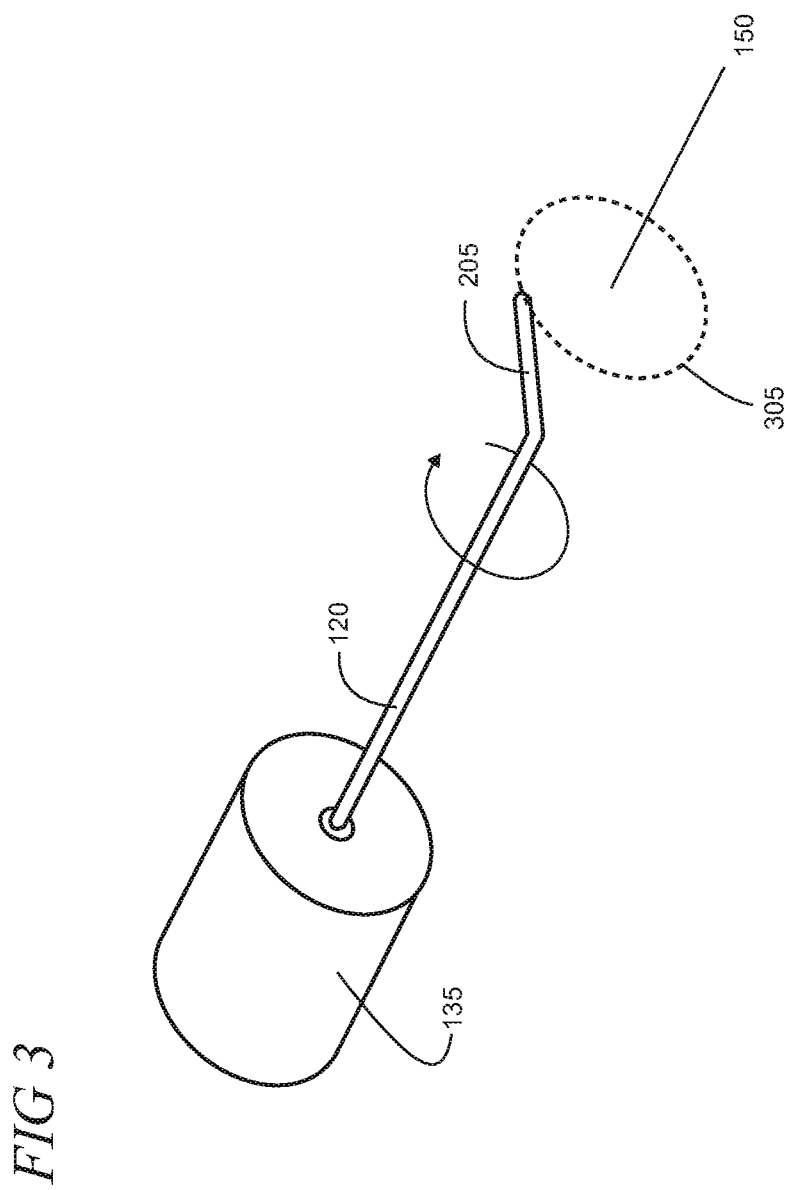
FIG. 3 shows a path traversed by a distal offset end of a driveshaft.

FIGS. 2A, 2B, 2C, and 2D sequentially show the driveshaft 120 as it rotates through one revolution when driven by the motor 135 (the motor, power source, and driveshaft are collectively referred to herein as a "drive assembly" as indicated by reference numeral 210). A proximal end of the driveshaft is coupled to the motor and a distal end has a portion 205 that is offset relative to the longitudinal axis 150 of the driveshaft. Thus, as shown in FIG. 3, the distal end of the driveshaft traverses a circular path 305 in a plane that is orthogonal to the longitudinal axis 150 as it is driven by the motor (note that the direction of rotation of the driveshaft shown in FIG. 3 is arbitrary).

Figure 4:
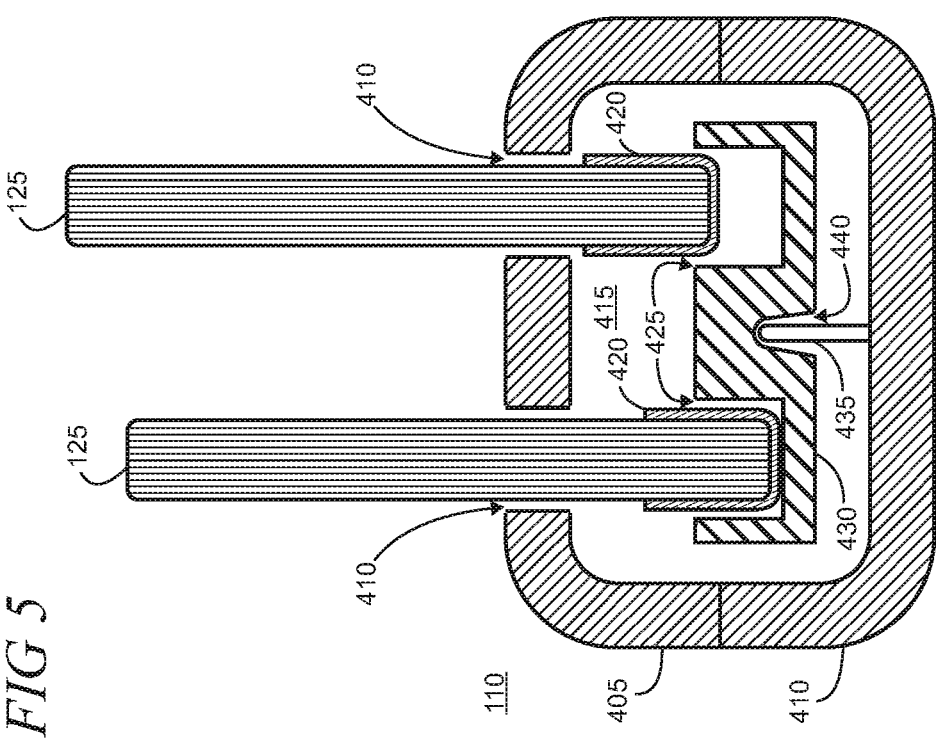
Figure 5:
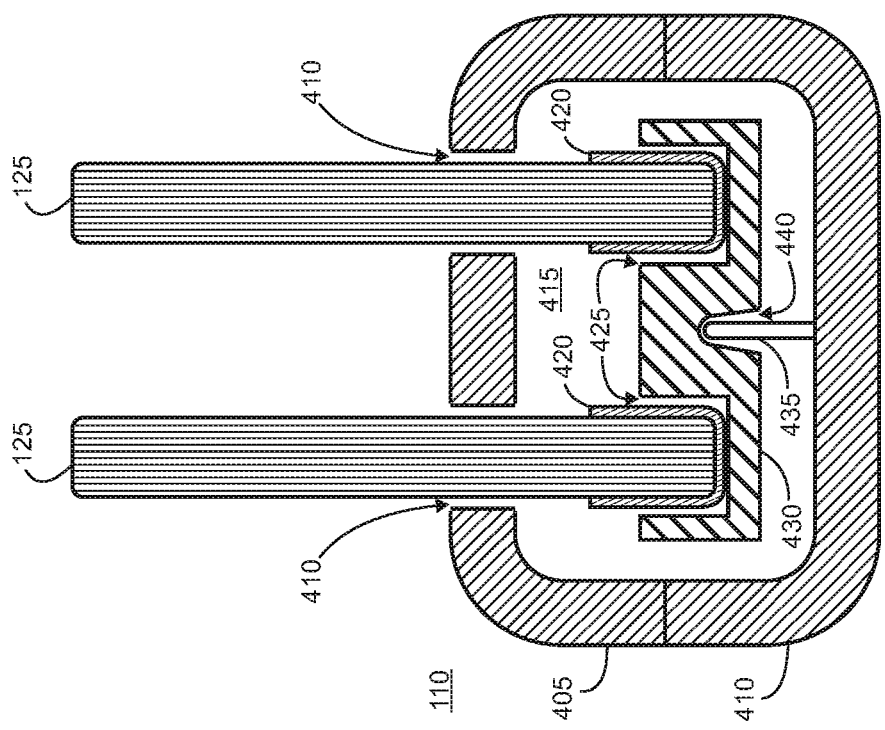

FIGS. 4 and 5 show the illustrative powered toothbrush 100 in a sectional view taken along A-A in FIG. 1. The head 110 of the toothbrush includes top shell 405 having perforations 410 and an opposing non-perforated bottom shell 406 (it is noted the terms such as "top," "bottom," "left," "right," "fore," "aft," "up," and "down" and the like are used primarily to establish relative orientations in the illustrative examples shown and described herein for ease of description). The top and bottom shells enclose an internal space 415 within the head. The top and bottom shells are configured in this illustrative example with flat surfaces that define respective parallel planes, however, other configurations can be selected to meet the needs of a particular toothbrush implementation.

The bristle tufts 125 are gathered together and fixedly attached to respective buckets 420 that circumferentially enclose the proximal ends of the tufts and have a solid bottom surface. The bristle tufts extend upwardly from openings in the bucket opposite the bottom surface such that their distal ends protrude through the perforation in the top shell 405. The distal ends of the bristle tufts are the primary teeth and gum cleaning elements in the present powered toothbrush.

The buckets 420 are non-fixedly located within respective bucket receiving recesses 425 in a movable plate 430 that is tiltably and rotatably coupled to a pivot 435 that extends upwards into the internal space 415 of the head 110 from the inside surface of the bottom shell 406. The pivot interfaces with a corresponding pivot receiving portion 440 in the movable plate. The pivot receiving portion may comprise a recess, as illustratively shown in the drawings, although a through hole, or another suitable interface with the pivot that enables the movable plate to tilt or rock and rotate with respect to the pivot may also be utilized. For example, the pivot and receiving interface may comprise a ball and socket joint, a multi-axis hinge, and other conventional mechanisms that allow for relative motion therewith with multiple DoF.

As shown in FIG. 5, the bucketed bristle tufts are captured within the internal space 415 of the toothbrush head 110 but are not otherwise fixedly attached to the movable plate 430 or any other structure or component of the powered toothbrush 100 (FIG. 1). While the outer bottom and side surfaces of the buckets 420 are configured to interface with the bucket receiving recesses 425 in the movable plate, the top circumferential edge of the bucket (i.e., the bucket's "rim") is configured as a stop that engages with the inside surface of the top shell 405 to limit axial excursion of the bristle tufts. Accordingly, the diameter of the bucket exceeds that of perforations in the top shell 405. In addition, the recesses are configured to provide gaps that are suitably sized to enable the buckets to freely move relative to the recesses including tilting, sliding, and rotating. In the illustrative embodiment shown, the bottom surfaces of the buckets and the opposing top surfaces of the recesses are both flat. In alternative embodiments, features such as wedges and other shapes may be utilized on the opposing surfaces to impart enhanced rotation to the buckets as they interface with the recesses during powered toothbrush operation.

FIGS. 6 and 7 show illustrative motion of bristle tufts 125 as the powered toothbrush is operated and the movable plate 430 tilts and rotates with respect to the pivot 435 in response to driveshaft rotation from the drive assembly 210 (FIG. 2). With each revolution of the driveshaft (not shown) the movable plate tilts to the left (FIG. 6) and to the right (FIG. 7). The moveable plate also tilts fore and aft with each driveshaft revolution and rotates and counter-rotates. The additional motions are shown in the remaining drawings and described in the accompanying text. The internal space 415 is configured to be larger than the maximum excursion of the movable plate. That is, there is a Z dimension, as indicated, between the moveable plate at its maximum excursion and the inside surface the top shell 405 to allow additional upward motion of the bucket 420 beyond that provided by the movable plate, as shown in FIG. 7. Accordingly, the bucketed bristle tufts can move with partial independence from the movable plate which can give rise to random bristle tuft motion during toothbrush operation.

The buckets 420 collide with the movable plate when the powered toothbrush is operated which causes the bristle tufts 125 to slideably move relative the perforations 410 in the top shell 405. As shown in the drawings, the motion can include axial motion along the longitudinal axis of the bristle tufts. In addition, the tilting of the movable plate causes the central axes of the cylindrically shaped bucket receiving recesses 425 and the cylindrically shaped perforations to become obliquely aligned. This can cause the bristle tufts to be extended with a tilted orientation relative to the top shell.

As noted above, the buckets have freedom of motion within the confines of the internal space 415 of the toothbrush head 110. While the collisions with the movable plate can impart an upward force to the bucketed bristle tufts, the toothbrush itself does not provide any mechanism to provide a restorative force to counter the outward motion. However, the contact between the distal ends of the bristle tufts and the user's teeth and gums tends to push the bristle tufts downward so that the buckets 420 re-engage with the movable plate. The cycle of upward projection and downward re-engagement can be expected to be non-periodic and irregular as the user brushes his or her teeth with the present powered toothbrush.

For example, a given bristle tuft may re-engage with the movable plate at any given point within its range of motion. For example, in one instance, the bucket may re-engage with the movable plate as it is tilting downwards. In other instances, the movable plate may be moving up, rotating, or counter-rotating. Accordingly, the bristle tufts have an overall motion that is random with multiple DoF. In some implementations, the randomness of the collisions may increase with increased rotational speed of the driveshaft. For example, when the toothbrush is operated at relatively high speed the movable plate behaves with vibratory motion and it collides with the buckets to thereby impart a sharp force. As the plane of the movable plate is not always parallel to the plane of the bucket's bottom surface, the point of contact between the movable plate and the bucket will vary which can further increase the randomness of bristle tuft motion.

FIGS. 8, 9, and 10 show the illustrative powered toothbrush 100 in a sectional view taken along B-B in FIG. 1. The moveable plate 430 is arranged in this illustrative example with long and short axes in which the long axis is parallel to the longitudinal axis of the driveshaft 205. A driveshaft receiving portion 805 of the movable plate is centrally located at the proximal end of the movable plate along the long axis. In alternative implementations, the driveshaft receiving portion can be offset from the center of the movable plate. An engagement feature 810 such as a guide, bearing, or pin is located at the offset distal end of the driveshaft 205. The engagement feature interfaces with the driveshaft receiving portion of the movable plate so that the end of the plate traverses the circular path 305 (FIG. 3) while the center of the plate tilts and rotates about the fixed pivot 435.

FIG. 8 shows the driveshaft 205 in an orientation in which its offset portion and non-offset portion collectively define a plane that is parallel to the top and bottom shells 405 and 406. FIG. 9 shows the driveshaft rotated 90 degrees from the driveshaft position shown in FIG. 8. FIG. 10 shows the driveshaft rotated 180 degrees from the driveshaft position shown in FIG. 9. As the driveshaft rotates during toothbrush operation, the movable plate 430 tilts fore and aft, as shown in FIGS. 9 and 10. It will be appreciated that driveshaft rotation causes cyclical motion of the movable plate whereby the left and right tilting shown in FIGS. 6 and 7 is superimposed on the fore and aft tilting shown in FIGS. 9 and 10. In addition to the tilting, cyclical rotating and counter-rotating motions of the movable plate about the pivot 435 also occur as the driveshaft rotates during toothbrush operation.

The range of motion of the movable plate 430 is illustrated in FIGS. 11A, 11B, 11C, and 11D. In these drawings, the movable plate 430 is represented in simplified form for clarity in exposition of the relationship between the longitudinal axis 1105 of the movable plate and a fixed central pivot point and the longitudinal axis 150 of the driveshaft. Axis 150 has the same orientation in each of the drawings which sequentially illustrate the position of the movable plate at the four cardinal points along the circular path 305 of the offset driveshaft portion. FIGS. 11A and 11D respectively show maximum fore and aft tilting of the movable plate. FIGS. 11B and 11C respectively show the movable plate with zero tilt (i.e., parallel to the top and bottom shells) and maximum rotation and counter-rotation about the pivot point. It will be appreciated that the side to side tilting of the movable plate occurs as the offset portion of the driveshaft rotates between the cardinal points.

The described embodiments have been described with certain words and phrases that attempt to describe certain motions. Motion can either be constant or vibratory. One example of a constant motion is simple rotation where an element angularly moves in a single direction (e.g., bristles which only rotate clockwise or swivel clockwise in a cone like envelope) or translates in a single direction. Vibration is any periodic movement having repeated cycles. Vibratory motion can have one or more frequencies and amplitudes. Vibratory movement which is substantially linear is referred to herein as a reciprocating motion. Reciprocating motion can occur in a number of directions, such as substantially horizontal, substantially vertical (i.e., a lifting or pulsating motion), and combinations thereof. Vibratory movement which is substantially rotational in nature is referred to herein as an oscillatory or pivoting motion.

Because most motions can be complex in nature (i.e., include elements of other types of motion), the use of the above-described terms herein can include other motions, unless stated otherwise (e.g., reciprocates only), in addition to the basic or primary motion described by the term. So, for example, a motion which is described herein as reciprocating may also include other vibratory or constant movements even though the primary movement is reciprocatory in nature.

The invention has been described with reference to particular embodiments. Modifications and alterations will occur to those skilled in the powered toothbrush arts upon reading and understanding this specification. For example, while certain elements have been described as comprising bends in a shaft and other cams have been described as including appropriately shaped beads secured to a shaft, the cams are not limited to the suggested form. Indeed, bends may be substituted for beads and beads may be substituted for bends. Where cams or cam portions are illustrated with one eccentricity or bent shape, multiple eccentricities, offset, or bent shapes may be included. Each added eccentricity, offset, or bent shape would increase the frequency with which the related bristle bucket vibrates, pulses, pivots, swivels, rocks, oscillates, reciprocates, or translates. Additionally, where multiple eccentricities or offsets are included, they may be of varying amplitude, thereby providing varying bristle tuft movement amplitudes. It is intended that all such modifications and alterations are included insofar as they come within the scope of the appended claims or equivalents thereof.

The subject matter described above is provided by way of illustration only and is not to be construed as limiting. Various modifications and changes may be made to the subject matter described herein without following the example embodiments and applications illustrated and described, and without departing from the true spirit and scope of the present invention, which is set forth in the following claims.

What is claimed:

1. A powered toothbrush, comprising:
   a handle having a neck;
   a head mounted to the neck and having a perforated shell and an opposed non-perforated shell that enclose an internal space within the head;
   a plurality of movable bristle tufts having distal ends that extend outwardly through perforations in the shell and proximal ends that are fixedly attached to a respective plurality of buckets, the buckets being captured within the internal space;
   a movable plate disposed in the internal space that includes recesses for non-fixedly receiving the buckets, the plate being rotatably and tiltably disposed on a pivot that extends into the internal space from an inside surface of the non-perforated shell; and
   a drive assembly operably connected to the movable plate, wherein the drive assembly tilts and rotates the movable plate with respect to the pivot during operation of the powered toothbrush,
   wherein the internal space and recesses are configured so that the bucketed bristle tufts are movable within the internal space,
   wherein each bucket includes a rim that is engageable with the perforated shell to stop movement of buckets beyond the internal space.

2. The powered toothbrush reeof claim 1, wherein the drive assembly comprises a motor coupled to a power source, and a rotatable driveshaft having a proximal end coupled to the motor and a distal end that has an offset portion relative to a longitudinal axis of the driveshaft.

3. The powered toothbrush of claim 2, wherein the movable plate includes a driveshaft receiving portion configured to receive the offset portion of the distal end of the driveshaft.

4. The powered toothbrush of claim 3, wherein the offset portion of the distal end of the driveshaft traverses a circular path in a plane that is orthogonal to the longitudinal axis of the driveshaft during operation of the powered toothbrush.

5. The powered toothbrush of claim 4 in which the driveshaft receiving portion of the movable plate traverses the circular path from engagement with the offset portion of the distal end of the driveshaft during operation of the powered toothbrush.

6. The powered toothbrush of claim 5 in which the movable plate has long and short axes and the driveshaft receiving portion of the movable plate is centered along the long axis of the movable plate.

7. The powered toothbrush of claim 6 in which the pivot engages with a pivot receiving hole in the movable plate that is located at an intersection between long and short axes of the movable plate.

8. The powered toothbrush of claim 1 in which a dimension of the internal space in which the bucketed bristles are movable exceeds a maximum excursion of the movable plate, the dimension being orthogonal to a longitudinal axis of the head and in a direction of the perforations.

9. The powered toothbrush of claim 1 in which the operation of the driveshaft causes vibratory motion of the movable plate such that the plate collides with the buckets to thereby impact random motion to the bristle tufts.

10. The powered toothbrush of claim 9 in which the random motion includes one or more of axial motion, rotational motion, or lateral motion of the bristle tufts.

11. The powered toothbrush of claim 1 further comprising a power source that is operatively coupled to a motor, or a power supply that is operatively coupled to the motor.

12. The powered toothbrush of claim 1 in which the tilting and rotating of the movable plate during toothbrush operation causes centers of the recesses in the movable plate and centers of the perforations to be cyclically obliquely and non-obliquely aligned.

13. The powered toothbrush of claim 1 in which the bucketed bristle tufts are slideably movable with respect to the recesses in the movable plate, and move independently from motion of the movable plate, and, wherein during powered toothbrush operation, the movable plate collides with the buckets to thereby impart random motion to the bristle tufts.

14. The powered toothbrush of claim 13 in which the bucketed bristle tufts are rotatably movable with respect to the recesses in the movable plate.

15. The powered toothbrush of claim 13 in which the buckets and recesses in the movable plate are cylindrical and diameters of buckets and recesses are respectively sized to provide a gap between the buckets and recesses, so that respective axes of the cylinders and recesses have cyclically parallel and non-parallel alignment during operation of the powered toothbrush.

16. The powered toothbrush of claim 15 in which the cyclical alignment is non-periodic.

17. The powered toothbrush of claim 15 in which the cyclical alignment is random.

18. The powered toothbrush of claim 13 in which a plane of a bottom surface of the buckets has randomly co-planar and non-co-planar alignment with a plane of surfaces of the recesses in the movable plate opposing the bottom surface of the buckets during operation of the powered toothbrush.

19. The powered toothbrush of claim 13 in which points of contact between bottom surfaces of the buckets and respective surfaces of the recesses in the movable plate opposing the bottom surfaces of the buckets vary as the movable plate and buckets collide during operation of the powered toothbrush.

20. The powered toothbrush of claim 19 in which the variation is random.

* * * * *